(12) United States Patent
Fusenig et al.

(10) Patent No.: US 7,838,510 B2
(45) Date of Patent: Nov. 23, 2010

(54) BIOMATERIALS BASED ON HYALURONIC ACID FOR THE ANTI-ANGIOGENIC THERAPY IN THE TREATMENT OF TUMORS

(75) Inventors: Norbert E. Fusenig, Heidelberg (DE); Hans-Jürgen Stark, Mecksheim (DE); Michael Willhauck, Mannheim (DE); Alessandra Pavesio, Padua (IT)

(73) Assignees: Fidia Farmaceutici S.P.A., Abano Terme (IT); Deutsches Krebsforschungszentrum, Heidelberg (DE)

( * ) Notice: Subject to any disclaimer, the term of this patent is extended or adjusted under 35 U.S.C. 154(b) by 729 days.

(21) Appl. No.: 10/501,030

(22) PCT Filed: Jan. 7, 2003

(86) PCT No.: PCT/EP03/00078

§ 371 (c)(1),
(2), (4) Date: Aug. 12, 2004

(87) PCT Pub. No.: WO03/057203

PCT Pub. Date: Jul. 17, 2003

(65) Prior Publication Data

US 2005/0037049 A1 Feb. 17, 2005

(30) Foreign Application Priority Data

Jan. 11, 2002 (IT) .......................... PD2002A0003

(51) Int. Cl.
*A61K 31/728* (2006.01)
*A61K 31/715* (2006.01)

(52) U.S. Cl. .......................... 514/54; 514/23; 536/55.1; 536/55.2; 536/123.1; 424/426

(58) Field of Classification Search .................. 514/54, 514/23; 536/55.1, 55.2, 123.1; 424/426
See application file for complete search history.

(56) References Cited

U.S. PATENT DOCUMENTS

| 4,851,521 | A | 7/1989 | Della Valle et al. |
| 5,520,916 | A | 5/1996 | Callegaro et al. |
| 6,872,819 | B1 * | 3/2005 | Pavesio et al. ............. 536/55.3 |

FOREIGN PATENT DOCUMENTS

| EP | 0341745 A | | 11/1989 |
| EP | 0466300 A | | 1/1992 |
| JP | 61000017 | * | 1/1986 |
| WO | WO 94/23725 | * | 10/1994 |
| WO | WO 97/07833 | * | 3/1997 |
| WO | WO 99/61080 A | | 12/1999 |
| WO | WO 00/01733 A | | 1/2000 |
| WO | WO 00/54762 A | | 9/2000 |
| WO | WO 00/57896 A | | 10/2000 |
| WO | WO 02/18448 A | | 3/2002 |
| WO | WO 02/18450 A | | 3/2002 |
| WO | WO 02/41877 A | | 5/2002 |

OTHER PUBLICATIONS

Derwent Abstract of Sakurai et al., JP 61000017, Jan. 6, 1986 (Abstract sent).*
STN Abstract of Sakurai et al., JP 61000017, Jan. 6, 1986 (Abstract sent).*
Berkeley et al. (Surgery, gynecology & obstetrics, (Mar. 1983) vol. 156, No. 3, pp. 319-22) (Abstract sent).*
Tonello et al. "In vitro reconstruction of human dermal equivalent enriched with endothelial cells" Biomaterials, vol. 24, No. 7, Mar. 7, 2003, pp. 1205-1211.
Glass et al. "A three-dimensional cell attachment matrix created by cross-linking RGD peptide modified hyaluronic acid" Journal of Cellular Biochemistry, Suppl. 19A, Jan. 5, 1996, p. 178.
Luo et al. "Cross-linked hyaluronic acid hydrogel films: new biomaterials for drug delivery" Journal of Controlled Release, vol. ,69, No. 1, Oct. 3, 2000, pp. 169-184.
Coradini et al. "Hyaluronic acid as drug delivery for sodium butyrate: improvement of the anti-proliferative activity on a breast-cancer cell line" International Journal of Cancer, vol. 81, No. 3, May 5, 1999, pp. 411-416.
Charrad, R. et al., "Ligation of the CD44 adhesion molecule reverses blockage of differentiation in human acute myeloid leukemia" Nature Medicine, vol. 5, No. 6, Jun. 1999, pp. 669-676.
Coradini, D. et al., "Hyaluronic Acid As Drug Delivery for Sodium Butyrate: Improvement of the Anti-Proliferative Activity on a Breast-Cancer Cell Line" Int. J. Cancer, vol. 81, 1999, pp. 411-416.
Freemantle, C. et al. "The Modulation of Granulomatous Tissue and Tumour Angiogenesis by Diclofenac in Combination With Hyaluronan (Hyal EX-0001)" Int. J. Tiss. Reac.,—vol. 27, No. 4, 1995, pp. 157-166.

(Continued)

*Primary Examiner*—Shaojia Anna Jiang
*Assistant Examiner*—Michael C Henry
(74) *Attorney, Agent, or Firm*—Birch, Stewart, Kolasch & Birch, LLP

(57) ABSTRACT

The use in the medical-surgical field of biomaterials based on hyaluronic acid derivatives, optionally in association with natural, synthetic or semisynthetic biopolymers, for suppressing the angiogenic process associated with tumor proliferation (in primary and secondary tumors) is disclosed.

11 Claims, 5 Drawing Sheets

OTHER PUBLICATIONS

Karasawa, Kenichiro et al., "Inhibition of experimental metastasis and cell adhesion of murine melanoma cells by chondroitin sulfate-derivatized lipid, a neoproteoglycan with anti-cell adhesion activity"Clinical & Experimental Metastasis, vol. 15, No. 2, 1997, pp. 83-93.

Salmon -EHR, V. et al., "Metastases Cutanees De Melanome Situees Sur Une Cicatrice De Prise De Greffe", Ann. Dermatol. Venereol., vol. 123, 1996, pp. 194-195.

Slevin, M. et al., "Angiogenic Oligosaccharides of Hyaluronan Induce Protein Tyrosine Kinase Activity in Endothelial Cells and Activate a Cytoplasmic Signal Transduction Pathway Resulting in Proliferation", Laboratory Investigation, vol. 78, No. 8, Aug. 1998, pp. 987-1003.

Hayen, Wiebke et al., "Hyaluronan stimulates tumor cell migration by modulating the fibrin fiber architecture", Journal of Cell Science, vol. 112, 1999, pp. 2241-2251.

Skobe, Mihaela et al., "Halting angiogenesis suppresses carcinoma cell invasion", Nature Medicine, vol. 3, No. 11, Nov. 1997, pp. 1222-1227.

* cited by examiner

A5            A5 Hyaff 11

4

6

II-4             II-4 Hyaff 11

4

6

II-4            II-4 Hyaff 11

1

2

4

6

II-4            II-4 Hyaff 11

4

6

BIOMATERIALS BASED ON HYALURONIC ACID FOR THE ANTI-ANGIOGENIC THERAPY IN THE TREATMENT OF TUMORS

This Application is the National Phase Under 35 U.S.C. §371 of PCT International. Application No. PCT/EP2003/00078 which has an International filing date of Jan. 7, 2003, which claims priority to Italian Application NO. PD2002A 00003 filed on Jan. 11, 2002. The entire contents of all applications listed above are hereby incorporated by reference.

SUBJECT OF THE INVENTION

The present invention relates to the use in the medical-surgical field of biomaterials based on hyaluronic acid derivatives, optionally in association with natural, synthetic or semisynthetic biopolymers, for suppressing the angiogenic process associated with tumour proliferation (in primary and secondary tumours).

BACKGROUND OF THE INVENTION

The induction and development of angiogenesis is a prerequisite for the development of a primary tumour, and for any subsequent metastases.

Angiogenesis is a dynamic process closely linked with the proliferation of cancer cells, because it is the latter that are chiefly responsible for the production and release of angiogenic factors, such as cytokines and other trophic factors. An increase in the vascularisation of a primary tumour can cause an increase in the number of cancer cells that enter into the circulation and give rise to new metastases.

Recent studies have demonstrated that an increase in the density of microvessels in an area affected by neoplasia indicates new tumour growth.

It is therefore clinically important to suppress angiogenesis to inhibit its development, if possible. Indeed, by associating anti-angiogenic therapy with "classic" anticancer therapy with drugs and/or radiation, with or without surgical removal of the tumour, it is possible to halt the proliferation of cancer cells, thus preventing the invasion of further tissues by said cells, and the consequent development of new metastases (Skobe H. et al., Nature Medicine, 1222-1227 (1997)).

In histological assessment of the onset of the angiogenic process associated with a cancerous growth, it is important to look for markers of the tumour's vascular system, for example with antibodies that differentiate the endothelial cells from the cancerous ones. For example, the anti-CD3 antibody is specific for marking the endothelial cells and therefore enables their identification in the angiogenic process associated with the development of new metastases. Its use has proved essential in assessing the level of microvessel development associated with neoplasia. Indeed, thanks to antibody marking, it is possible to visualise and count the number of interconnections of the vessels within the cancerous tissue to understand and quantify the angiogenic process, relating it to any new developments in the neoplasia (thereby deciding if/how much/how to associate a therapy that modulates or inhibits angiogenesis with an established/classic anticancer therapy.

One such therapy consists in administering drugs that act by blocking the receptors of the trophic factors (PGDF, bFGF, VEGF) that are also angiogenic factors.

Preclinical results 'in vivo' have shown that said drugs prove important in inhibiting tumour growth but they do not determine regression of the tumour itself: on the strength of these major experimental data, the drugs have been introduced in numerous clinical trials.

However, an anti-angiogenic clinical therapy that provides for a generally oral pharmacological administration in chronic form may have many toxic side effects, because angiogenesis is not only associated with pathological disorders but also physiological processes such as tissue reproduction and repair ("*Cancer: Principle Practice of Oncology*" V. De Vita, S. Hellmann and S. Rosenberg, 6$^{th}$ Edition).

It is therefore of strategic importance to associate classic anticancer therapy with an anti-angiogenic therapy "in situ", and this is the subject of the present invention.

Hyaluronic acid is one of the chief components of the extracellular matrix of the connective tissue, and there are numerous scientific publications concerning its role in various processes, both physiological and pathological, such as the formation of granulation tissue, chemotaxis in the inflammatory process, cell differentiation for various cell types. Other studies concern its role within the family of "substrate adhesion molecules".

Hyaluronic acid has been used for the above indications:
- as a differentiating agent in therapy for acute myeloid leukaemia (Charrad R. S. et al., Nature Medicine 5, 669-676 (1999));
- as a vehicle for drugs such as steroids or NSAIDs, antibiotics and anti-neoplastic agents, because of the abundant expression of its receptor (CD44) in cancer cells; (Freemantle, C. et al., Int. J. Tiss. Reac. XVIII (4) 157-166 (1995); Coradini, D. et al., Int. J. Cancer 5, 411-416 (1999));
- in preclinical studies on the inhibition of lung metastasis, because of its capacity for inhibiting the adhesion of cancer cells to the vascular endothelium (Karasaza K. et al., Clinical & Experimental Metastasis 15, 83-93 (1997));
- as a means of controlling adhesion to the substrate with subsequent proliferation of cells (possibly also cancer cells) permanently "in situ" after surgical removal of tissues (including tumours) (U.S. Pat. No. 5,627,162).

Experimental observations "in vivo" have, however, revealed that hyaluronic acid may have a chemotaxic activity on cancer cells within the granulation tissue that forms after removal of cutaneous metastasis of melanoma (Salmon-Ehr, V. et al., Ann. Dermatol. Venereol, 123, 194-195 (1996)). Moreover, numerous pre-clinical studies have demonstrated that hyaluronic acid enhances cancer cell migration, thereby favouring metastasis, as it is known that the degradation products of hyaluronic acid, that is, oligosaccharides constituted by 10 and 20 oligomers, are strong inducers of the angiogenic process (Hayen et al., J. Cell. Sci. 112, 2241-2251 (1999); Slevin, M. et al., Lab. Invest. 78 (8), 987-1003 (1998)).

Moreover, biomaterials based on hyaluronic acid and/or the derivatives thereof have never been used as an anti-angiogenic therapy, neither have any other biodegradable and/or non-biodegradable biopolymers ever been used in anticancer therapies.

Absolutely innovative, therefore, is the use of biomaterials based on hyaluronic acid derivatives such as Hyaff® (EP 0 216 453 B1) or ACPs (EP 0 341 745 B1) in the form of non-woven felts for instance (EP0 618 817 B1) or as three-dimensional structures (WO 99/61080), possibly in association with various biomaterials (e.g. natural ones such as collagen, cellulose, polysaccharides, chitin, chitosan, pectin, agar, gellan and alginic acid, synthetic ones such as polylactic acid (PLA), polyglycolic acid (PGA), polyurethanes and polysulphonic resins, or semisynthetic ones such as collagen cross-linked with aldehyde, diamine and gellan) as a therapy to suppress and/or inhibit the angiogenic process that enhances and determines tumour metastasis.

DETAILED DESCRIPTION OF THE INVENTION

The present invention relates to biomaterials based on hyaluronic acid derivatives made into non-woven felts (as the preferred form of biomaterial), optionally in association with natural, synthetic or semisynthetic biopolymers, for use in the medical-surgical field as a new anti-angiogenic therapy ("in situ"), optionally associated with classic pharmacological anticancer therapies and/or radiotherapy, to modulate indirectly the proliferation of tumours, thus blocking the formation of local relapses and, therefore, any new metastases.

In order to study, characterise and then assess "in vivo" the effect of the biomaterial of the present invention in the angiogenic process that supports the development of skin carcinomas (considered to be a clarifying example), the Applicant has developed a new model of tumour/stromal cell support interaction, described as follows:
1) two cell lines of human keratinocytes transfected with the ras-oncogene: HACaT II-4, malignant variant and A5, benign variant;
2) said cells are transferred onto a collagen gel mounted into teflon rings covered by a silicone chamber, known as the Fusenig silicone chamber (FSC);
3) said FSC is then placed over the muscle fascia of the backs of nude mice, in the presence or absence of an immediately underlying layer of biomaterial based on Hyaff® 11 (total benzyl ester of hyaluronic acid) made in the form of a non-woven felt;
4) four to six weeks later, two different types of granulation tissue will have formed underneath the cancerous epithelium;
5) the development of the epithelial tumour and of the underlying granulation tissue is assessed, over time, both by classic histological analyses (haematoxylin/eosin) and by immunohistochemical techniques using the anti-CD31 antibody, to visualise the presence of vascular epithelium and therefore determine the development of the angiogenic process;
6) the levels of cellular proliferation are examined using immunohistochemical techniques associated with the introduction of BrdU into the DNA of proliferating cells, both within the granulation tissue underneath the epithelium and in the cancerous epithelium itself. Marking with the anti-integrin α6 antibody was also assessed to study the level of cellular proliferation within the cancerous epithelium.

Figure 1:
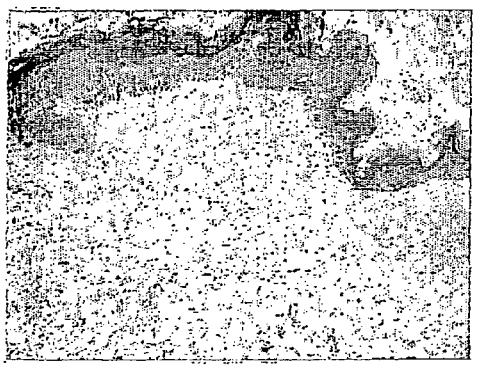
FIGS. 1-4 show the results of immunohistochemical tissue examinations.
Figure 1:
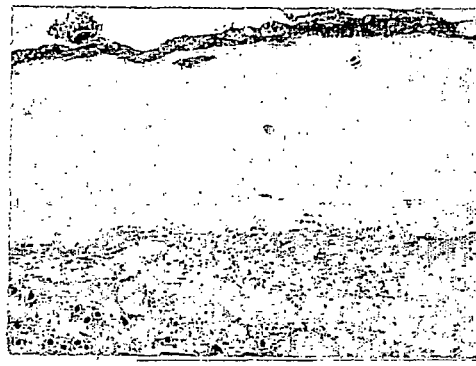
Figure 1:
Figure 1:
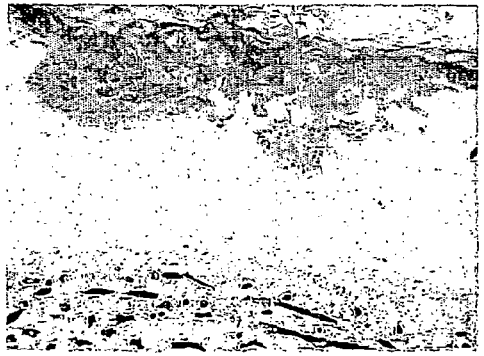

The results of the experiment were as follows:

HACaT A5 line:

After 4-6 weeks, the cancerous epithelium in the control FSC (i.e. without any biomaterial placed under the epithelium), was well developed and multilayered, while the layer of granulation tissue underneath had completely replaced the layer of collagen that separated the epithelium from the underlying tissue (FIG. 1).

Conversely, four weeks later, the cancerous epithelium in the FSC placed over the Hyaff®-based biomaterial in the form of a non-woven felt is less developed than the relative control, and the layer of collagen that separates it from the nascent granulation tissue underneath is still thick and not infiltrated by cells and/or vessels (FIG. 1).

After six weeks, the quantity of collagen is still abundant, with just an initial layer of granulation tissue that begins to form over the biomaterial (FIG. 1).

Figure 2:
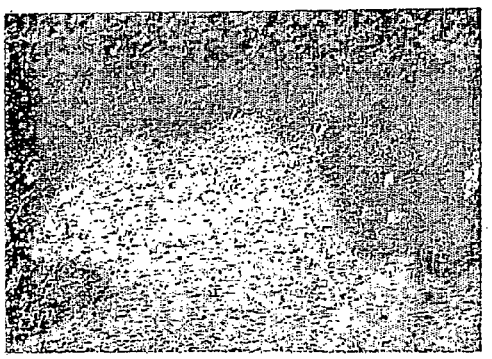
Figure 2:
Figure 2:
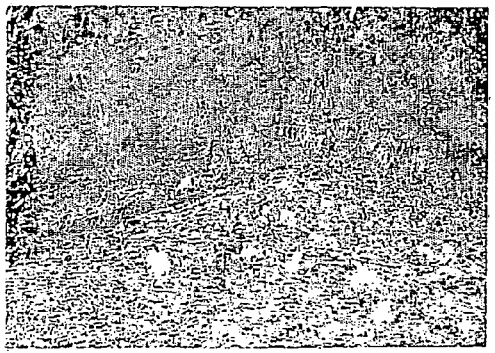
Figure 2:
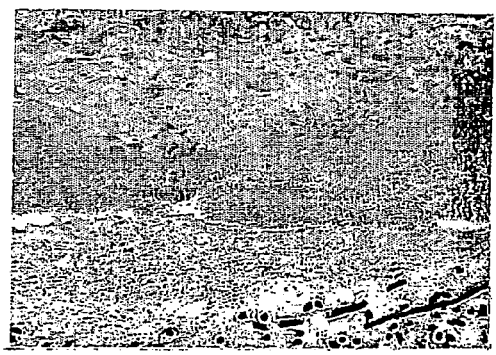

HACaT II 4 Line:

After four to six weeks, in the control FSC, the cancer cells have constituted a thick epithelium that penetrates into the thickness of the new granulation tissue underneath, that has already completely replaced the layer of collagen that separated it from the epithelium (FIG. 2).

Four weeks later, in the FSC placed over the Hyaff®-based biomaterial, the cancerous epithelium is thin but easily distinguishable from the granulation tissue forming over the biomaterial, separated from this tissue by the collagen gel that is still present and not yet absorbed (FIG. 2).

Six weeks later, the tumour mass and the granulation tissue have established close contact, but there has been no actual infiltration of tumour cells into the granulation tissue, unlike the control, where the tumour cells have completely invaded the new, underlying granulation tissue (FIG. 2).

Figure 3:
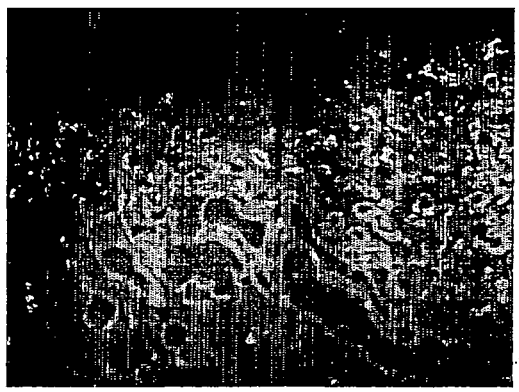
Figure 3:
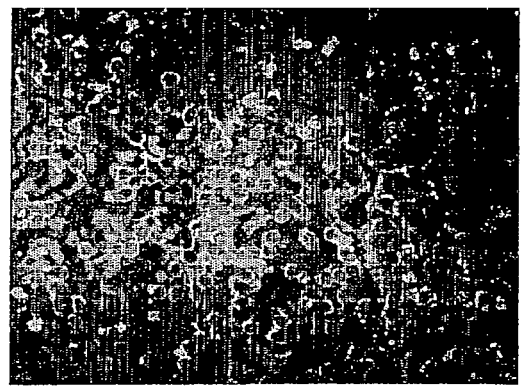
Figure 3:
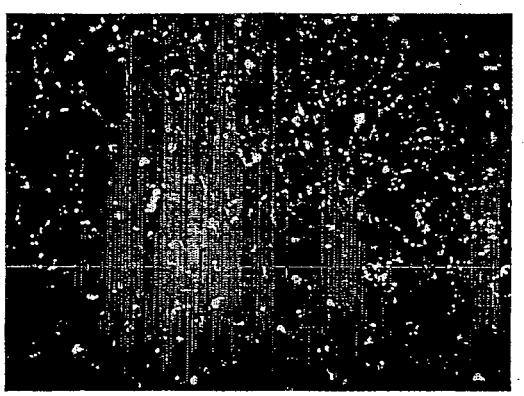
Figure 3:
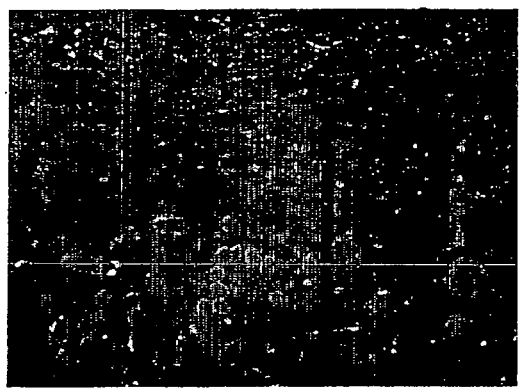
Figure 3:
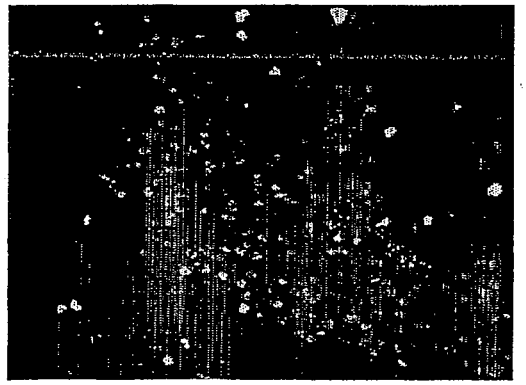
Figure 3:
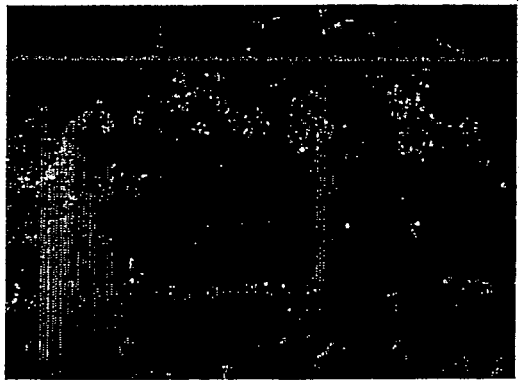
Figure 3:
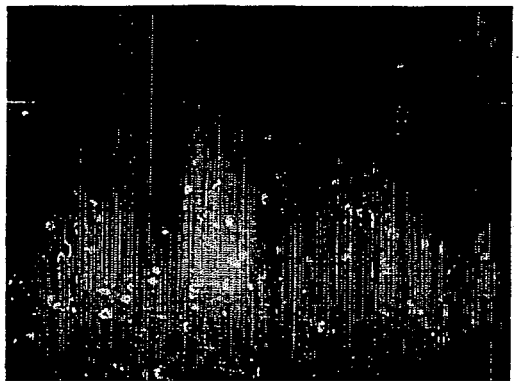
Figure 3:
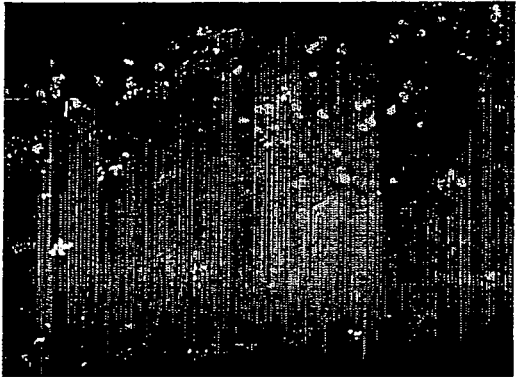

Using immunohistochemical techniques linked with the specific marking of particular nucleotides such as BrdU, at the $1^{st}$ and $2^{nd}$ weeks, good cell proliferation is evident within the nascent granulation tissue in the control and in the Hyaff®-based biomaterial, while at 4, and especially at 6, weeks after transplant, the cell growth rate drops drastically in the granulation tissue underneath the cancerous epithelium, which conversely maintains in both samples a good level of cellular proliferation (FIG. 3).

The growth of cancerous epithelium can also be visualised with a specific antibody against the protein integrin α6. Said molecule is, indeed, a component of the hemidesmosomes and its expression is normally only associated with the proliferative area of the epithelial layers.

Figure 3A:
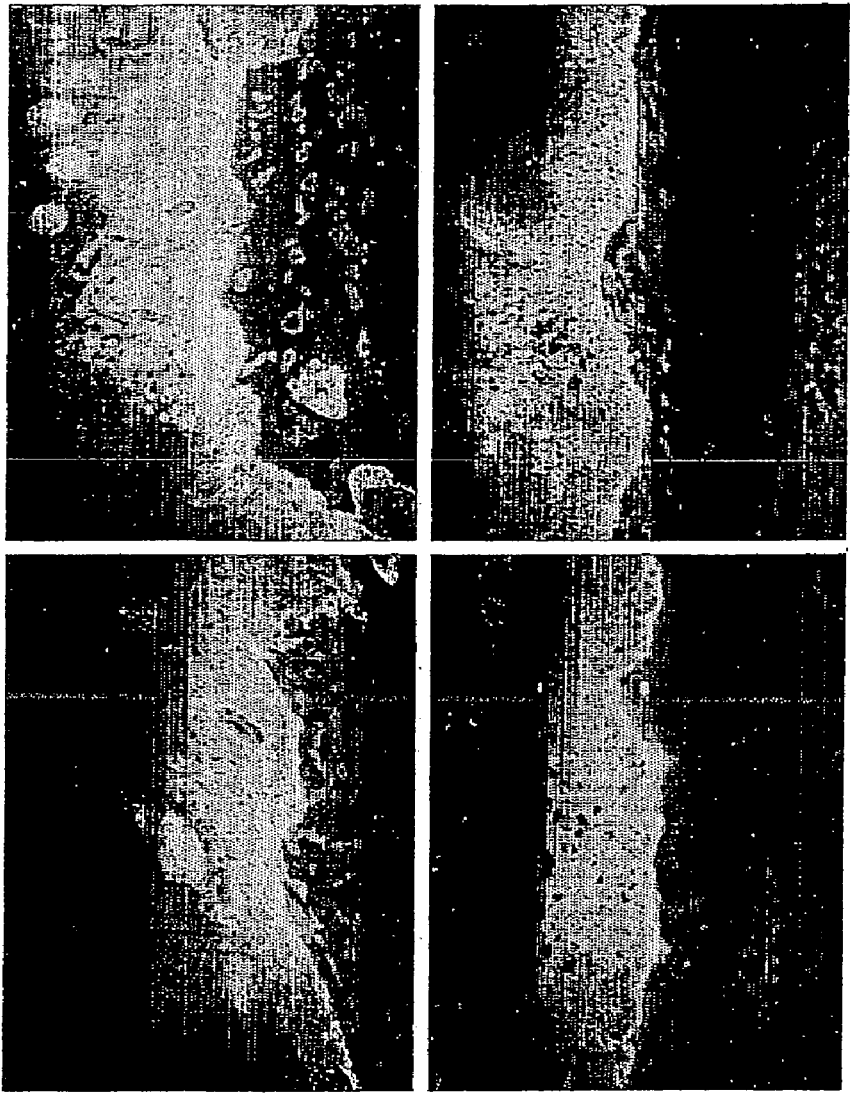

FIG. 3a shows that antibody marking for the integrin protein α6 is notably present throughout the cancerous epithelium both in the control FCS and in the FCS with the Hyaff®-based biomaterial, even though expression of the test protein appears less extensive throughout the thickness of the cancerous epithelium in the latter sample.

Figure 4:
Figure 4:
Figure 4:
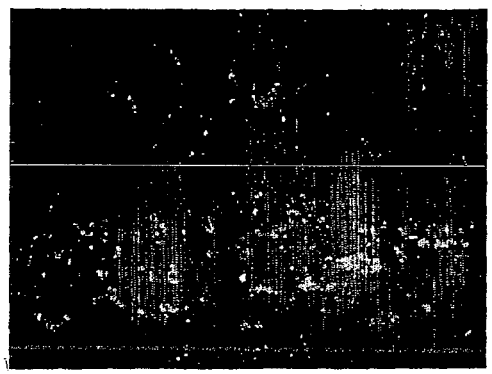
Figure 4:
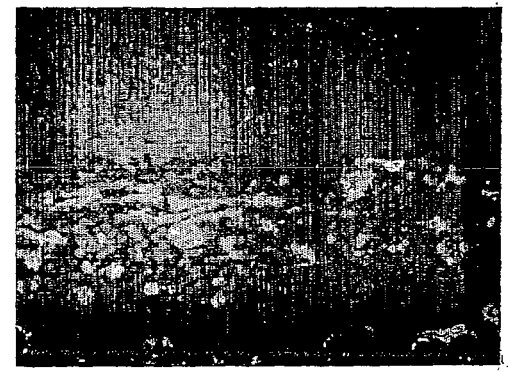

Specific marking for the vascular epithelium with the anti-CD31 antibody reveals, furthermore, that in the controls, after four weeks, the angiogenic process is well established as the vessels in the underlying granulation tissue already reach the cancerous epithelium and after 6 weeks they invade it, thus favouring metastasis (FIG. 4).

In the case of the FSC with the Hyaff®-based biomaterial, after four weeks there is still no close contact between granulation tissue and cancerous epithelium. This will occur only after six weeks, even though there is no invasion of the epithelium by the underlying microvessels, that remain relegated to the granulation tissue (FIG. 4).

The angiogenic process seems to be at a standstill, no longer enhancing tumour development. Vascularisation is limited to the area covered by the Hyaff®-based biomaterial, so the tumour cells do not invade the granulation tissue that has formed within the biomaterial.

In conclusion, the Hyaff®-based biomaterial proved able to modulate/inhibit the angiogenic process related to vascularisation of the cancerous epithelium. It therefore proves to be particularly advantageous to use the biomaterials based on hyaluronic acid derivatives in the oncological field, where it is important to modulate the angiogenic process and therefore, indirectly, the proliferation of cancer cells in primary and secondary tumours.

According to the invention, the biomaterials that can be useful in the oncological field as a new anti-angiogenic therapy "in situ" may be, for example, in the form of non-woven felts, sponges, films, membranes, microspheres or in other three-dimensional forms in cases where it is necessary to fill the cavities that are liable to form after surgical removal of a tumour.

The anti-angiogenic action of the biomaterial can, moreover, be supported by supplementing the biomaterial with NSAIDs, steroids, hormones, antibiotics and especially anti-cancer drugs such as fluorouracil, methotrexate, cis-platinum, carboplatin, oxaliplatin, ethopoxide, cyclophosphamide, vincristine, doxorubicin.

The invention being thus described, it is clear that these methods can be modified in various ways. Said modifications are not to be considered as divergences from the spirit and purposes of the invention and any modification that would appear evident to an expert in the field comes within the scope of the following claims.

The invention claimed is:

1. A method for the treatment of a patient having a primary or secondary tumor by inhibiting angiogenesis, comprising applying at the tumor site of said patient a biomaterial comprised of a benzyl ester of hyaluronic acid wherein said hyaluronic acid is a total benzyl ester of hyaluronic acid, wherein said hyaluronic acid is 100% benzyl esterified and wherein said biomaterial inhibits angiogenic processes related to vascularization by granulation tissue forming over the biomaterial and wherein said biomaterial is in the form of at least one member selected from the group consisting of a non-woven felt, sponge, microsphere, film and membrane.

2. The method according to claim 1 wherein said hyaluronic acid is in association with other natural, synthetic and/or semisynthetic biopolymers.

3. The method according to claim 2, wherein the natural biopolymer is selected from the group consisting of collagen, cellulose, polysaccharides, chitin, chitosan, pectins, agar, gellan and alginic acid.

4. The method according to claim 2, wherein the synthetic biopolymer is selected from the group consisting of polylactic acid (PLA), polyglycolic acid (PGA), polyurethanes and polysulphonic resins.

5. The method according to claim 2, wherein the semisynthetic biopolymer is selected from the group consisting of collagen cross-linked with aldehydes, diamine and gellan.

6. The method according to claim 1 wherein the biomaterial further comprises with at least one pharmacologically active substance.

7. The method according to claim 6, wherein the pharmacologically active substance is selected from the group consisting of fluorouracil, methotrexate, cis-platinum, carboplatin, oxaliplatin, ethopoxide, cyclophosphamide, vincristine, and doxorubicin.

8. The method according to claim 1, wherein said biomaterial is applied to the tumor site by filling a cavity resulting from the surgical removal of a tumor.

9. The method of claim 1, wherein the vascularisation is limited to the area covered by the biomaterial, so that the tumor cells do not invade the granulation tissue that has formed within the biomaterial.

10. A method for the treatment of a patient having a primary or secondary tumor by modulating the proliferation of tumors by inhibiting angiogenesis, comprising applying at the tumor site of said patient a biomaterial comprised of a benzyl ester of hyaluronic acid wherein said benzyl ester of hyaluronic acid is a total benzyl ester of hyaluronic acid, wherein said hyaluronic acid is 100% benzyl esterified and wherein said biomaterial inhibits angiogenic processes related to vascularization by granulation tissue forming over the biomaterial and wherein said biomaterial is in the form of at least one member selected from the group consisting of a non-woven felt, sponge, microsphere, film and membrane.

11. A method for the treatment of a patient having a primary or secondary tumor by inhibiting angiogenesis associated with tumor proliferation, comprising applying at the tumor site a biomaterial comprised of a benzyl ester of hyaluronic acid wherein said benzyl ester of hyaluronic acid is a total benzyl ester of hyaluronic acid, wherein said hyaluronic acid is 100% benzyl esterified and wherein said biomaterial inhibits angiogenic processes related to vascularization by granulation tissue forming over the biomaterial and wherein said biomaterial is in the form of at least one member selected from the group consisting of a non-woven felt, sponge, microsphere, film and membrane.

* * * * *